US 6,403,094 B1

(12) United States Patent
Titball et al.

(10) Patent No.: US 6,403,094 B1
(45) Date of Patent: Jun. 11, 2002

(54) CLOSTRIDIUM PERFRINGENS VACCINES

(75) Inventors: Richard W Titball; Ethel D Williamson; Helen L Havard; Petra C F Oyston; Dean W Payne, all of Salisbury (GB)

(73) Assignee: The Secretary of State for Defence in Her Britannic Majesty's Government of the United Kingdom of Great Britain and Northern Ireland, Farnborough (GB)

( * ) Notice: Subject to any disclaimer, the term of this patent is extended or adjusted under 35 U.S.C. 154(b) by 0 days.

(21) Appl. No.: 09/142,584

(22) PCT Filed: Mar. 11, 1997

(86) PCT No.: PCT/GB97/00660

§ 371 (c)(1),
(2), (4) Date: Sep. 11, 1998

(87) PCT Pub. No.: WO97/34001

PCT Pub. Date: Sep. 18, 1997

(30) Foreign Application Priority Data

Mar. 12, 1996 (GB) .............................. 9605222

(51) Int. Cl.[7] ................ A61K 39/02; A61K 39/00; A61K 39/385; A61K 39/08; C07K 1/00
(52) U.S. Cl. ................ 424/190.1; 424/192.1; 424/197.11; 424/234.1; 424/236.1; 424/239.1; 424/247.1; 530/350; 530/403; 530/820; 530/825
(58) Field of Search ................ 530/350, 420, 530/403, 808, 820, 825; 435/243, 822, 842; 514/1, 2, 773; 424/190.1, 192.1, 197.11, 234.1, 236.1, 239.1, 247.1

(56) References Cited

U.S. PATENT DOCUMENTS 895,073 A * 8/1908 Sterne
5,272,256 A * 12/1993 Bloch
5,817,317 A * 10/1998 Titball et al.

FOREIGN PATENT DOCUMENTS

GB 895 073 A 5/1962

OTHER PUBLICATIONS

Titball et al. The role of histidine residues in the alphatorin.*
George et al Macromol Sequency Synthesis, Select Meth Appl pp. 127–149. Alan Liss Inc., 1988.*
Rudinger et al. "Peptide Hormones" edited by Parsons University Park Press, pp. 6–7, Jun. 1976.*
Lazar et al (Molecullar & Cellular Biology vol. 8(3) pp.1247–1252), Mar. 1988.*
Burgess et al (J. Of Cell Biology vol. 111 pp. 2129–2138), Nov. 1990.*
Salgaller et al (Cancer Immunol. Immunothes. vol. 39 pp. 105–116), 1994.*
Infection and Immunity, vol. 60, No. 1, Jan. 1992, pp. 102–110, XP000674523 Hunter S.E. et al.: "cloning and nucleotide sequencing of the clostridium perfringens epsilon–toxin gene and its expression in *escherichia coli.* ".
Fems Microbiology Letters, vol. 41, 1987, pp. 317–319, XP000674521 Sakurai J. and Nagahama M.: "Histidine residues in Clostridium perfringens epsilon toxin.".
Fems Microbiology Letters, vol. 68, 1990, pp. 261–265, XP000674531 Titball R.W. and Rubidge T.: "The role of histidine residues in the alpha toxin of Clostridium perfringens.".

* cited by examiner

*Primary Examiner*—Mark Navarro
(74) *Attorney, Agent, or Firm*—Nixon & Vanderhye P.C.

(57) ABSTRACT

The present invention provides proteins for use in vaccines which are capable of inducing protective antibodies directed against *C. perfringens* epsilon toxin when administered to animals or man and thereby providing prophylaxis or therapy against infection by *C. perfringens* epsilon toxin. Particularly the present invention provides proteins which are based upon the mature toxin of the *clostridium perfringens* epsilon toxin gene, but which have a mutation such that the amino acid at position 106 is different to the wild-type sequence and their use in vaccine compositions.

3 Claims, 1 Drawing Sheet

Fig. 1.

EPSILON TOXIN — SIGNAL SEQUENCE PROTOTOXIN — MATURE TOXIN pGEXetx.10A IN pGEX.3X — ptac — GLUTATHIONE-S-TRANSFERASE — MATURE TOXIN

EXPRESSES FUSION

GST-SDM10 FUSION — GLUTATHIONE-S-TRANSFERASE — MATURE TOXIN pTrcetx.10A IN pTrc99A — ptrc — SIGNAL SEQUENCE PROTOTOXIN — MATURE TOXIN

EXPRESSES FULL LENGTH EPSILON

SDM10 — SIGNAL SEQUENCE PROTOTOXIN — MATURE TOXIN

SEQUENCE LISTING

```
<160> NUMBER OF SEQ ID NOS: 6

<210> SEQ ID NO 1
<211> LENGTH: 987
<212> TYPE: DNA
<213> ORGANISM: Clostridium perfringens
<220> FEATURE:
<221> NAME/KEY: mat_peptide
<222> LOCATION: (136)..(456)
<220> FEATURE:
<221> NAME/KEY: misc_signal
<222> LOCATION: (1)..(32)
<220> FEATURE:
<221> NAME/KEY: CDS
<222> LOCATION: (1)..(984)

<400> SEQUENCE: 1 atg aaa aaa aat ctt gta aaa agt tta gca a tc gca tca gcg gtg ata      48
Met Lys Lys Asn Leu Val Lys Ser Leu Ala I le Ala Ser Ala Val Ile
-45                 -40                 -35                 -30
```

-continued

| | | |
|---|---|---|
| tcc atc tat tca ata gtt aat att gtt tca c ca act aat gta ata gct<br>Ser Ile Tyr Ser Ile Val Asn Ile Val Ser P ro Thr Asn Val Ile Ala<br>                -25                        -20                        -15 | 96 | aag gaa ata tct aat aca gta tct aat gaa a tg tcc aaa aaa gct tct        144
Lys Glu Ile Ser Asn Thr Val Ser Asn Glu M et Ser Lys Lys Ala Ser
            -10                 -5                 -1   1 tat gat aat gta gat aca tta att gag aaa g ga aga tat aat aca aaa        192
Tyr Asp Asn Val Asp Thr Leu Ile Glu Lys G ly Arg Tyr Asn Thr Lys
         5                  10                 15 tat aat tac tta aag aga atg gaa aaa tat t at cct aat gct atg gca        240
Tyr Asn Tyr Leu Lys Arg Met Glu Lys Tyr T yr Pro Asn Ala Met Ala
 20              25                  30                  35 tat ttt gat aag gtt act ata aat cca caa g ga aat gat ttt tat att        288
Tyr Phe Asp Lys Val Thr Ile Asn Pro Gln G ly Asn Asp Phe Tyr Ile
             40                  45                  50 aat aat cct aaa gtt gaa tta gat gga gaa c ca tca atg aat tat ctt        336
Asn Asn Pro Lys Val Glu Leu Asp Gly Glu P ro Ser Met Asn Tyr Leu
             55                  60                  65 gaa gat gtt tat gtt gga aaa gct ctc tta a ct aat gat act caa caa        384
Glu Asp Val Tyr Val Gly Lys Ala Leu Leu T hr Asn Asp Thr Gln Gln
         70                  75                  80 gaa caa aaa tta aaa tca caa tca ttc act t gt aaa aat act gat aca        432
Glu Gln Lys Leu Lys Ser Gln Ser Phe Thr C ys Lys Asn Thr Asp Thr
 85                  90                  95 gta act gca act act act cat act gtg gga a ct tcg ata caa gca act        480
Val Thr Ala Thr Thr Thr His Thr Val Gly T hr Ser Ile Gln Ala Thr
100                 105                 110                 115 gct aag ttt act gtt cct ttt aat gaa aca g ga gta tca tta act act        528
Ala Lys Phe Thr Val Pro Phe Asn Glu Thr G ly Val Ser Leu Thr Thr
             120                 125                 130 agt tat agt ttt gca aat aca aat aca aat a ct aat tca aaa gaa att        576
Ser Tyr Ser Phe Ala Asn Thr Asn Thr Asn T hr Asn Ser Lys Glu Ile
             135                 140                 145 act cat aat gtc cct tca caa gat ata cta g ta cca gct aat act act        624
Thr His Asn Val Pro Ser Gln Asp Ile Leu V al Pro Ala Asn Thr Thr
         150                 155                 160 gta gaa gta ata gca tat tta aaa aaa gtt a at gtt aaa gga aat gta        672
Val Glu Val Ile Ala Tyr Leu Lys Lys Val A sn Val Lys Gly Asn Val
165                 170                 175 aag tta gta gga caa gta agt gga agt gaa t gg gga gag ata cct agt        720
Lys Leu Val Gly Gln Val Ser Gly Ser Glu T rp Gly Glu Ile Pro Ser
180                 185                 190                 195 tat tta gct ttt cct agg gat ggt tat aaa t tt agt tta tcg gat aca        768
Tyr Leu Ala Phe Pro Arg Asp Gly Tyr Lys P he Ser Leu Ser Asp Thr
             200                 205                 210 gta aat aag agt gat tta aat gaa gat ggt a ct att aat att aat gga        816
Val Asn Lys Ser Asp Leu Asn Glu Asp Gly T hr Ile Asn Ile Asn Gly
             215                 220                 225 aaa gga aat tat agt gca gtt atg gga gat g ag tta ata gtt aag gtt        864
Lys Gly Asn Tyr Ser Ala Val Met Gly Asp G lu Leu Ile Val Lys Val
             230                 235                 240 aga aat tta aat aca aat aat gta caa gaa t at gta ata cct gta gat        912
Arg Asn Leu Asn Thr Asn Asn Val Gln Glu T yr Val Ile Pro Val Asp
         245                 250                 255 aaa aaa gaa aaa agt aat gat tca aat ata g ta aaa tat agg agt ctt        960
Lys Lys Glu Lys Ser Asn Asp Ser Asn Ile V al Lys Tyr Arg Ser Leu
260                 265                 270                 275 tat att aag gca cca gga ata aaa taa                                     987
Tyr Ile Lys Ala Pro Gly Ile Lys

280

<210> SEQ ID NO 2
<211> LENGTH: 328
<212> TYPE: PRT
<213> ORGANISM: Clostridium perfringens

<400> SEQUENCE: 2

Met Lys Lys Asn Leu Val Lys Ser Leu Ala Ile Ala Ser Ala Val Ile
-45                 -40                 -35                 -30

Ser Ile Tyr Ser Ile Val Asn Ile Val Ser Pro Thr Asn Val Ile Ala
            -25                 -20                 -15

Lys Glu Ile Ser Asn Thr Val Ser Asn Glu Met Ser Lys Lys Ala Ser
            -10                  -5                  -1   1

Tyr Asp Asn Val Asp Thr Leu Ile Glu Lys Gly Arg Tyr Asn Thr Lys
        5                   10                  15

Tyr Asn Tyr Leu Lys Arg Met Glu Lys Tyr Tyr Pro Asn Ala Met Ala
    20                  25                  30                  35

Tyr Phe Asp Lys Val Thr Ile Asn Pro Gln Gly Asn Asp Phe Tyr Ile
                40                  45                  50

Asn Asn Pro Lys Val Glu Leu Asp Gly Glu Pro Ser Met Asn Tyr Leu
                55                  60                  65

Glu Asp Val Tyr Val Gly Lys Ala Leu Leu Thr Asn Asp Thr Gln Gln
        70                  75                  80

Glu Gln Lys Leu Lys Ser Gln Ser Phe Thr Cys Lys Asn Thr Asp Thr
        85                  90                  95

Val Thr Ala Thr Thr Thr His Thr Val Gly Thr Ser Ile Gln Ala Thr
100                 105                 110                 115

Ala Lys Phe Thr Val Pro Phe Asn Glu Thr Gly Val Ser Leu Thr Thr
                120                 125                 130

Ser Tyr Ser Phe Ala Asn Thr Asn Thr Asn Ser Lys Glu Ile
                135                 140                 145

Thr His Asn Val Pro Ser Gln Asp Ile Leu Val Pro Ala Asn Thr Thr
        150                 155                 160

Val Glu Val Ile Ala Tyr Leu Lys Lys Val Asn Val Lys Gly Asn Val
165                 170                 175

Lys Leu Val Gly Gln Val Ser Gly Ser Glu Trp Gly Glu Ile Pro Ser
180                 185                 190                 195

Tyr Leu Ala Phe Pro Arg Asp Gly Tyr Lys Phe Ser Leu Ser Asp Thr
                200                 205                 210

Val Asn Lys Ser Asp Leu Asn Glu Asp Gly Thr Ile Asn Ile Asn Gly
                215                 220                 225

Lys Gly Asn Tyr Ser Ala Val Met Gly Asp Glu Leu Ile Val Lys Val
        230                 235                 240

Arg Asn Leu Asn Thr Asn Asn Val Gln Glu Tyr Val Ile Pro Val Asp
    245                 250                 255

Lys Lys Glu Lys Ser Asn Asp Ser Asn Ile Val Lys Tyr Arg Ser Leu
260                 265                 270                 275

Tyr Ile Lys Ala Pro Gly Ile Lys
                280

<210> SEQ ID NO 3
<211> LENGTH: 987
<212> TYPE: DNA
<213> ORGANISM: Clostridium perfringens
<220> FEATURE:

-continued

```
<221> NAME/KEY: mat_peptide
<222> LOCATION: (136)..(987)
<220> FEATURE:
<221> NAME/KEY: misc_signal
<222> LOCATION: (1)..(32)
<220> FEATURE:
<221> NAME/KEY: CDS
<222> LOCATION: (1)..(984)

<400> SEQUENCE: 3
```

| | | | | | | | | | | | | | | | |
|---|---|---|---|---|---|---|---|---|---|---|---|---|---|---|---|
| atg | aaa | aaa | aat | ctt | gta | aaa | agt | tta | gca | a tc | gca | tca | gcg | gtg | ata | 48 |
| Met | Lys | Lys | Asn | Leu | Val | Lys | Ser | Leu | Ala | I le | Ala | Ser | Ala | Val | Ile | |
| -45 | | | | -40 | | | | -35 | | | | -30 | | | | |
| tcc | atc | tat | tca | ata | gtt | aat | att | gtt | tca | c ca | act | aat | gta | ata | gct | 96 |
| Ser | Ile | Tyr | Ser | Ile | Val | Asn | Ile | Val | Ser | P ro | Thr | Asn | Val | Ile | Ala | |
| | | | -25 | | | | | -20 | | | | | -15 | | | |
| aag | gaa | ata | tct | aat | aca | gta | tct | aat | gaa | a tg | tcc | aaa | aaa | gct | tct | 144 |
| Lys | Glu | Ile | Ser | Asn | Thr | Val | Ser | Asn | Glu | M et | Ser | Lys | Lys | Ala | Ser | |
| | | | -10 | | | | | -5 | | | | | -1 | 1 | | |
| tat | gat | aat | gta | gat | aca | tta | att | gag | aaa | g ga | aga | tat | aat | aca | aaa | 192 |
| Tyr | Asp | Asn | Val | Asp | Thr | Leu | Ile | Glu | Lys | G ly | Arg | Tyr | Asn | Thr | Lys | |
| | 5 | | | | | 10 | | | | | 15 | | | | | |
| tat | aat | tac | tta | aag | aga | atg | gaa | aaa | tat | t at | cct | aat | gct | atg | gca | 240 |
| Tyr | Asn | Tyr | Leu | Lys | Arg | Met | Glu | Lys | Tyr | T yr | Pro | Asn | Ala | Met | Ala | |
| 20 | | | | | 25 | | | | | 30 | | | | | 35 | |
| tat | ttt | gat | aag | gtt | act | ata | aat | cca | caa | g ga | aat | gat | ttt | tat | att | 288 |
| Tyr | Phe | Asp | Lys | Val | Thr | Ile | Asn | Pro | Gln | G ly | Asn | Asp | Phe | Tyr | Ile | |
| | | | 40 | | | | | 45 | | | | | 50 | | | |
| aat | aat | cct | aaa | gtt | gaa | tta | gat | gga | gaa | c ca | tca | atg | aat | tat | ctt | 336 |
| Asn | Asn | Pro | Lys | Val | Glu | Leu | Asp | Gly | Glu | P ro | Ser | Met | Asn | Tyr | Leu | |
| | | | 55 | | | | | 60 | | | | | 65 | | | |
| gaa | gat | gtt | tat | gtt | gga | aaa | gct | ctc | tta | a ct | aat | gat | act | caa | caa | 384 |
| Glu | Asp | Val | Tyr | Val | Gly | Lys | Ala | Leu | Leu | T hr | Asn | Asp | Thr | Gln | Gln | |
| | | 70 | | | | | 75 | | | | | 80 | | | | |
| gaa | caa | aaa | tta | aaa | tca | caa | tca | ttc | act | t gt | aaa | aat | act | gat | aca | 432 |
| Glu | Gln | Lys | Leu | Lys | Ser | Gln | Ser | Phe | Thr | C ys | Lys | Asn | Thr | Asp | Thr | |
| | | 85 | | | | | 90 | | | | | 95 | | | | |
| gta | act | gca | act | act | act | ccg | act | gtg | gga | a ct | tcg | ata | caa | gca | act | 480 |
| Val | Thr | Ala | Thr | Thr | Thr | Pro | Thr | Val | Gly | T hr | Ser | Ile | Gln | Ala | Thr | |
| 100 | | | | | 105 | | | | | 110 | | | | | 115 | |
| gct | aag | ttt | act | gtt | cct | ttt | aat | gaa | aca | g ga | gta | tca | tta | act | act | 528 |
| Ala | Lys | Phe | Thr | Val | Pro | Phe | Asn | Glu | Thr | G ly | Val | Ser | Leu | Thr | Thr | |
| | | | 120 | | | | | 125 | | | | | 130 | | | |
| agt | tat | agt | ttt | gca | aat | aca | aat | aca | aat | a ct | aat | tca | aaa | gaa | att | 576 |
| Ser | Tyr | Ser | Phe | Ala | Asn | Thr | Asn | Thr | Asn | T hr | Asn | Ser | Lys | Glu | Ile | |
| | | | 135 | | | | | 140 | | | | | 145 | | | |
| act | cat | aat | gtc | cct | tca | caa | gat | ata | cta | g ta | cca | gct | aat | act | act | 624 |
| Thr | His | Asn | Val | Pro | Ser | Gln | Asp | Ile | Leu | V al | Pro | Ala | Asn | Thr | Thr | |
| | | | 150 | | | | | 155 | | | | | 160 | | | |
| gta | gaa | gta | ata | gca | tat | tta | aaa | aaa | gtt | a at | gtt | aaa | gga | aat | gta | 672 |
| Val | Glu | Val | Ile | Ala | Tyr | Leu | Lys | Lys | Val | A sn | Val | Lys | Gly | Asn | Val | |
| | 165 | | | | | 170 | | | | | 175 | | | | | |
| aag | tta | gta | gga | caa | gta | agt | gga | agt | gaa | t gg | gga | gag | ata | cct | agt | 720 |
| Lys | Leu | Val | Gly | Gln | Val | Ser | Gly | Ser | Glu | T rp | Gly | Glu | Ile | Pro | Ser | |
| 180 | | | | | 185 | | | | | 190 | | | | | 195 | |
| tat | tta | gct | ttt | cct | agg | gat | ggt | tat | aaa | t tt | agt | tta | tcg | gat | aca | 768 |
| Tyr | Leu | Ala | Phe | Pro | Arg | Asp | Gly | Tyr | Lys | P he | Ser | Leu | Ser | Asp | Thr | |
| | | | 200 | | | | | 205 | | | | | 210 | | | |
| gta | aat | aag | agt | gat | tta | aat | gaa | gat | ggt | a ct | att | aat | att | aat | gga | 816 |
| Val | Asn | Lys | Ser | Asp | Leu | Asn | Glu | Asp | Gly | T hr | Ile | Asn | Ile | Asn | Gly | |
| | | | 215 | | | | | 220 | | | | | 225 | | | |

-continued

```
aaa gga aat tat agt gca gtt atg gga gat g ag tta ata gtt aag gtt    864
Lys Gly Asn Tyr Ser Ala Val Met Gly Asp G lu Leu Ile Val Lys Val
            230                 235                 240 aga aat tta aat aca aat aat gta caa gaa t at gta ata cct gta gat    912
Arg Asn Leu Asn Thr Asn Asn Val Gln Glu T yr Val Ile Pro Val Asp
        245                 250                 255 aaa aaa gaa aaa agt aat gat tca aat ata g ta aaa tat agg agt ctt    960
Lys Lys Glu Lys Ser Asn Asp Ser Asn Ile V al Lys Tyr Arg Ser Leu
260                 265                 270                 275 tat att aag gca cca gga ata aaa taa                                 987
Tyr Ile Lys Ala Pro Gly Ile Lys
                280
```

<210> SEQ ID NO 4
<211> LENGTH: 328
<212> TYPE: PRT
<213> ORGANISM: Clostridium perfringens

<400> SEQUENCE: 4

```
Met Lys Lys Asn Leu Val Lys Ser Leu Ala I le Ala Ser Ala Val Ile
-45                 -40                 -35                 -30

Ser Ile Tyr Ser Ile Val Asn Ile Val Ser P ro Thr Asn Val Ile Ala
            -25                 -20                 -15

Lys Glu Ile Ser Asn Thr Val Ser Asn Glu M et Ser Lys Lys Ala Ser
        -10                  -5                  -1   1

Tyr Asp Asn Val Asp Thr Leu Ile Glu Lys G ly Arg Tyr Asn Thr Lys
     5                   10                  15

Tyr Asn Tyr Leu Lys Arg Met Glu Lys Tyr T yr Pro Asn Ala Met Ala
20                  25                  30                  35

Tyr Phe Asp Lys Val Thr Ile Asn Pro Gln G ly Asn Asp Phe Tyr Ile
            40                  45                  50

Asn Asn Pro Lys Val Glu Leu Asp Gly Glu P ro Ser Met Asn Tyr Leu
        55                  60                  65

Glu Asp Val Tyr Val Gly Lys Ala Leu Leu T hr Asn Asp Thr Gln Gln
    70                  75                  80

Glu Gln Lys Leu Lys Ser Gln Ser Phe Thr C ys Lys Asn Thr Asp Thr
85                  90                  95

Val Thr Ala Thr Thr Pro Thr Val Gly Thr S er Ile Gln Ala Thr
100                 105                 110                 115

Ala Lys Phe Thr Val Pro Phe Asn Glu Thr G ly Val Ser Leu Thr Thr
            120                 125                 130

Ser Tyr Ser Phe Ala Asn Thr Asn Thr Asn T hr Asn Ser Lys Glu Ile
        135                 140                 145

Thr His Asn Val Pro Ser Gln Asp Ile Leu V al Pro Ala Asn Thr Thr
    150                 155                 160

Val Glu Val Ile Ala Tyr Leu Lys Lys Val A sn Val Lys Gly Asn Val
165                 170                 175

Lys Leu Val Gly Gln Val Ser Gly Ser Glu T rp Gly Glu Ile Pro Ser
180                 185                 190                 195

Tyr Leu Ala Phe Pro Arg Asp Gly Tyr Lys P he Ser Leu Ser Asp Thr
            200                 205                 210

Val Asn Lys Ser Asp Leu Asn Glu Asp Gly T hr Ile Asn Ile Asn Gly
        215                 220                 225

Lys Gly Asn Tyr Ser Ala Val Met Gly Asp G lu Leu Ile Val Lys Val
    230                 235                 240

Arg Asn Leu Asn Thr Asn Asn Val Gln Glu T yr Val Ile Pro Val Asp
```

```
                245                 250                 255
Lys Lys Glu Lys Ser Asn Asp Ser Asn Ile V al Lys Tyr Arg Ser Leu
260                 265                 270                 275

Tyr Ile Lys Ala Pro Gly Ile Lys
            280

<210> SEQ ID NO 5
<211> LENGTH: 987
<212> TYPE: DNA
<213> ORGANISM: Clostridium perfringens
<220> FEATURE:
<221> NAME/KEY: mat_peptide
<222> LOCATION: (136)..(987)
<220> FEATURE:
<221> NAME/KEY: misc_signal
<222> LOCATION: (1)..(32)
<220> FEATURE:
<221> NAME/KEY: CDS
<222> LOCATION: (1)..(984)
<220> FEATURE:
<223> OTHER INFORMATION: "n" at positions 451-453 represent a, t, c,
      g or other

<400> SEQUENCE: 5 atg aaa aaa aat ctt gta aaa agt tta gca a tc gca tca gcg gtg ata        48
Met Lys Lys Asn Leu Val Lys Ser Leu Ala I le Ala Ser Ala Val Ile
-45                 -40                 -35                 -30 tcc atc tat tca ata gtt aat att gtt tca c ca act aat gta ata gct        96
Ser Ile Tyr Ser Ile Val Asn Ile Val Ser P ro Thr Asn Val Ile Ala
            -25                 -20                 -15 aag gaa ata tct aat aca gta tct aat gaa a tg tcc aaa aaa gct tct       144
Lys Glu Ile Ser Asn Thr Val Ser Asn Glu M et Ser Lys Lys Ala Ser
        -10                 -5                  -1  1 tat gat aat gta gat aca tta att gag aaa g ga aga tat aat aca aaa       192
Tyr Asp Asn Val Asp Thr Leu Ile Glu Lys G ly Arg Tyr Asn Thr Lys
    5                   10                  15 tat aat tac tta aag aga atg gaa aaa tat t at cct aat gct atg gca       240
Tyr Asn Tyr Leu Lys Arg Met Glu Lys Tyr T yr Pro Asn Ala Met Ala
 20                  25                  30                  35 tat ttt gat aag gtt act ata aat cca caa g ga aat gat ttt tat att       288
Tyr Phe Asp Lys Val Thr Ile Asn Pro Gln G ly Asn Asp Phe Tyr Ile
                40                  45                  50 aat aat cct aaa gtt gaa tta gat gga gaa c ca tca atg aat tat ctt       336
Asn Asn Pro Lys Val Glu Leu Asp Gly Glu P ro Ser Met Asn Tyr Leu
            55                  60                  65 gaa gat gtt tat gtt gga aaa gct ctc tta a ct aat gat act caa caa       384
Glu Asp Val Tyr Val Gly Lys Ala Leu Leu T hr Asn Asp Thr Gln Gln
        70                  75                  80 gaa caa aaa tta aaa tca caa tca ttc act t gt aaa aat act gat aca       432
Glu Gln Lys Leu Lys Ser Gln Ser Phe Thr C ys Lys Asn Thr Asp Thr
    85                  90                  95 gta act gca act act act nnn act gtg gga a ct tcg ata caa gca act       480
Val Thr Ala Thr Thr Thr Xaa Thr Val Gly T hr Ser Ile Gln Ala Thr
100                 105                 110                 115 gct aag ttt act gtt cct ttt aat gaa aca g ga gta tca tta act act       528
Ala Lys Phe Thr Val Pro Phe Asn Glu Thr G ly Val Ser Leu Thr Thr
                120                 125                 130 agt tat agt ttt gca aat aca aat aca aat a ct aat tca aaa gaa att       576
Ser Tyr Ser Phe Ala Asn Thr Asn Thr Asn T hr Asn Ser Lys Glu Ile
            135                 140                 145 act cat aat gtc cct tca caa gat ata cta g ta cca gct aat act act       624
Thr His Asn Val Pro Ser Gln Asp Ile Leu V al Pro Ala Asn Thr Thr
        150                 155                 160
```

```
gta gaa gta ata gca tat tta aaa aaa gtt a at gtt aaa gga aat gta      672
Val Glu Val Ile Ala Tyr Leu Lys Lys Val A sn Val Lys Gly Asn Val
    165                 170                 175 aag tta gta gga caa gta agt gga agt gaa t gg gga gag ata cct agt      720
Lys Leu Val Gly Gln Val Ser Gly Ser Glu T rp Gly Glu Ile Pro Ser
180             185                 190                 195 tat tta gct ttt cct agg gat ggt tat aaa t tt agt tta tcg gat aca      768
Tyr Leu Ala Phe Pro Arg Asp Gly Tyr Lys P he Ser Leu Ser Asp Thr
                200                 205                 210 gta aat aag agt gat tta aat gaa gat ggt a ct att aat att aat gga      816
Val Asn Lys Ser Asp Leu Asn Glu Asp Gly T hr Ile Asn Ile Asn Gly
            215                 220                 225 aaa gga aat tat agt gca gtt atg gga gat g ag tta ata gtt aag gtt      864
Lys Gly Asn Tyr Ser Ala Val Met Gly Asp G lu Leu Ile Val Lys Val
        230                 235                 240 aga aat tta aat aca aat aat gta caa gaa t at gta ata cct gta gat      912
Arg Asn Leu Asn Thr Asn Asn Val Gln Glu T yr Val Ile Pro Val Asp
    245                 250                 255 aaa aaa gaa aaa agt aat gat tca aat ata g ta aaa tat agg agt ctt      960
Lys Lys Glu Lys Ser Asn Asp Ser Asn Ile V al Lys Tyr Arg Ser Leu
260             265                 270                 275 tat att aag gca cca gga ata aaa taa                                   987
Tyr Ile Lys Ala Pro Gly Ile Lys
                280

<210> SEQ ID NO 6
<211> LENGTH: 328
<212> TYPE: PRT
<213> ORGANISM: Clostridium perfringens

<400> SEQUENCE: 6

Met Lys Lys Asn Leu Val Lys Ser Leu Ala I le Ala Ser Ala Val Ile
-45                 -40                 -35                 -30

Ser Ile Tyr Ser Ile Val Asn Ile Val Ser P ro Thr Asn Val Ile Ala
            -25                 -20                 -15

Lys Glu Ile Ser Asn Thr Val Ser Asn Glu M et Ser Lys Lys Ala Ser
        -10                  -5                  -1   1

Tyr Asp Asn Val Asp Thr Leu Ile Glu Lys G ly Arg Tyr Asn Thr Lys
     5                  10                  15

Tyr Asn Tyr Leu Lys Arg Met Glu Lys Tyr T yr Pro Asn Ala Met Ala
 20                  25                  30                  35

Tyr Phe Asp Lys Val Thr Ile Asn Pro Gln G ly Asn Asp Phe Tyr Ile
                 40                  45                  50

Asn Asn Pro Lys Val Glu Leu Asp Gly Glu P ro Ser Met Asn Tyr Leu
             55                  60                  65

Glu Asp Val Tyr Val Gly Lys Ala Leu Leu T hr Asn Asp Thr Gln Gln
         70                  75                  80

Glu Gln Lys Leu Lys Ser Gln Ser Phe Thr C ys Lys Asn Thr Asp Thr
     85                  90                  95

Val Thr Ala Thr Thr Xaa Thr Val Gly T hr Ser Ile Gln Ala Thr
100                 105                 110                 115

Ala Lys Phe Thr Val Pro Phe Asn Glu Thr G ly Val Ser Leu Thr Thr
                120                 125                 130

Ser Tyr Ser Phe Ala Asn Thr Asn Thr T hr Asn Ser Lys Glu Ile
             135                 140                 145

Thr His Asn Val Pro Ser Gln Asp Ile Leu V al Pro Ala Asn Thr Thr
         150                 155                 160
```

-continued

```
Val Glu Val Ile Ala Tyr Leu Lys Lys Val Asn Val Lys Gly Asn Val
    165                 170                 175

Lys Leu Val Gly Gln Val Ser Gly Ser Glu Trp Gly Glu Ile Pro Ser
180                 185                 190                 195

Tyr Leu Ala Phe Pro Arg Asp Gly Tyr Lys Phe Ser Leu Ser Asp Thr
                200                 205                 210

Val Asn Lys Ser Asp Leu Asn Glu Asp Gly Thr Ile Asn Ile Asn Gly
            215                 220                 225

Lys Gly Asn Tyr Ser Ala Val Met Gly Asp Glu Leu Ile Val Lys Val
            230                 235                 240

Arg Asn Leu Asn Thr Asn Asn Val Gln Glu Tyr Val Ile Pro Val Asp
    245                 250                 255

Lys Lys Glu Lys Ser Asn Asp Ser Asn Ile Val Lys Tyr Arg Ser Leu
260                 265                 270                 275

Tyr Ile Lys Ala Pro Gly Ile Lys
                280
```

CLOSTRIDIUM PERFRINGENS VACCINES

The present application is a U.S. national phase of PCT/GB97/00660, filed Mar. 11, 1997, which claims the benefit of GB 9605222.0, filed Mar. 12, 1996.

The present invention relates to novel peptides capable of eliciting an immunological response that is protective against *Clostridium perfringens* epsilon toxin in man or animals. It relates to the production of these peptides and to pharmaceutical compositions containing them, Preferred agents enable prophylaxis and treatment of *Clostridium perfringens* induced disease states in both humans and other animals.

*Clostridium perfringens* (*C. perfringens*) is ubiquitous in the environment and has been found in the soil, decaying organic matter and as part of the gut flora in man and animals. Different strains of *C. perfringens* can be assigned to one of five biotypes (A–E) depending on the spectrum of types produced see McDonel, J. L. (1986); Toxins of *Clostridium perfringens* types A,B,C,D and E. *In Pharmacology of Bacterial Toxins*; F. Dorner and J. Drews, eds. (Oxford: Pergamon Press), pp. 477–517. The epsilon toxin is produced by *C. perfringens* types B and D but not by types A, C or E see Brooks, M. E., Sterne, M., and Warrack, G. H. (1957); A reassessment of the criteria used for type differentiation of *Clostridia perfringens*. *J. Pathol. Bacteriol.* 74, 185–195. *C. perfringens* types B and D have a limited host range being mainly isolated from goats and cattle and rarely from man, Smith, L. D. and Williams, B. L. (1984); *The pathogenic anaerobic bacteria* (Springfield, Ill.: Charles C. Thomas). They are responsible for producing severe and rapidly fatal enterotoxaemia: *C. perfringens* type B enterotoxaemia infection of lambs causes lamb dysentery while type D enterotoxaemia produces pulpy kidney disease in sheep and lambs. Mortality rates in both cases may be as high as 100%. Neither disease is infectious, but sporadic outbreaks occur when the microbial balance of the gut is disrupted, for example after antibiotic treatment or due to changes in diet. Pulpy kidney disease is often associated with a change from a poor to a rich diet accompanied by excessive over-eating, Bullen, J. J. (1970); Role of toxins in host-parasite relationships. *In Micribial toxins volume 1*. S. Ajl, S. Kadis, and T. C. Montie, eds. (New York: Academic Press), pp. 233–276. Such over-eating causes considerable quantities of undigested, starch-rich food to pass from the rumen into the small intestine. The nutritious anaerobic environment this produces allows the multiplication of *C. perfringens* resulting in up to $10^9$ cfu per g of ileal contents and high concentrations of epsilon toxin Bullen, J. J. and Scarisbrick, R. (1957); Enterotoxaemia of sheep: experimental reproduction of the disease; *J. Pathol. Bacteriol.* 73, 494–509. Several vaccines exist for the prevention of *C. perfringens* enterotoxaemia. The vaccines are based on formaldehyde-treated cell filtrates or whole cell cultures. The vaccines confer a high degree of protection in animals Stephen, J. and Pietrowski, R. A. (1986); Bacterial toxins (England: van Nostrand Reinhold (UK) Co. Ltd.); however, the immunogenicity of the epsilon toxin in the preparations has been reported to be variable and a more defined and consistent vaccine is preferable. Immunity to a single epitope on the toxin has been shown to be sufficient to protect against purified epsilon toxin and *C. perfringens* infection, Percival, D. A., Shuttleworth, A. D., Williamson, E. D., and Kelly, D. C. (1990), Anti-idiotypic antibody-induced protection against *Clostridium perfringens* type D; *Infect. Immun.* 58, 2487–2492.

Epsilon toxin is produced by *C. perfringens* types B and D as a relatively inactive prototoxin of 311 amino acids with a molecular weight of 32,700, Worthington, R. W. and Mulders, M. S. (1977); Physical changes in the epsilon prototoxin molecule of *Clostridium perfringens* during enzymatic activation; *Infect. Immun.* 18, 549–551. Proteolytic cleavage of 13 or 14 basic amino acids from the amino terminal of the prototoxin results in the production of the mature toxin with a molecular weight of 31,200 Worthington and Mulders, 1977; Hunter, S. E., Clarke, I. N., Kelly, D. C., and Titball, R. W. (1992); Cloning and nucleotide sequencing of the *Clostridium perfringens* epsilon-toxin gene and its expression in *Escherichia coli; Infect. Immun.* 60, 102–110. Activation also results in a marked shift in pI from 8.02 (prototoxin) to either 5.36 (fully active toxin) or 5.74 (partially active toxin) and a significant change in conformation (Worthington and Mulders, 1977; Habeeb, A. F., Lee, C. L., and Atassi, M. Z. (1973); Conformational studies on modified proteins and peptides, VII; Conformation of epsilon-prototoxin and epsilon-toxin from *Clostridium perfringens*; Conformational changes associated with toxicity; *Biochim. Biophys. Acta* 322, 245–250). A complication is that the activation of the prototoxin seems to produce several isoforms with a range of specific activities between that of the prototoxin and the mature toxin (Habeeb, A. F. (1975); Studies on epsilon-prototoxin of *Clostridium perfringens* type D. Physicochemical and chemical properties of epsilon-prototoxin; *Biochim. Biophys. Acta* 412, 62–69; Worthington and Mulders, 1977). More recently it has been found that the toxin itself also has several isoforms (Hunter et al., 1992). Thus activation of epsilon prototoxin may be a multi-step process, possibly with multiple proteolytic cleavages and post-translational modifications such as deamination and phosphorylation resulting in the production of the heterogeneous mature toxin (Hunter et al., 1992).

Epsilon toxin is usually obtained from a type D strain of *C. perfringens* and has been purified either individually or in combination by methanol precipitation, ammonium sulphate precipitation, column chromatography, size exclusion and various forms of ion exchange chromatography (Verwoerd, D. W. (1960); *Isolation van die protoksien van Clostidium welchii type D. J. S. Afr. Vet. Med. Assoc.* 31, 195–203; Habeeb, A. F. (1969); Studies on epsilon-prototoxin of *Clostridium perfringens* type D. I. Purification methods: evidence for multiple forms of epsilon-prototoxin; *Arch. Biochem. Biophys.* 130, 430–440; Worthington, R. W., Mulders, M. S., and Van Rensburg, J. J. (1973); *Clostridium perfringens* type D epsilon prototoxin. Some chemical, immunological and biological properties of a highly purified prototoxin; *Onderstepoort. J. Vet. Res.* 40, 143–149; Payne, D. W., Williamson, E. D., Havard, H., Modi, N., and Brown, J. (1994); Evaluation of a new cytotoxicity assay for *Clostridium perfringens* type D epsilon toxin; *FEMS Microbiol. Lett.* 116, 161–167).

Traditionally, the activity of purified epsilon toxin has been determined in mouse lethality tests (Habeeb, A. F. (1969); Studies on epsilon-prototoxin of *Clostridium perfringens* type D. I. Purification methods: evidence for multiple forms of epsilon-prototoxin; *Arch. Biochem. Biophys.* 130, 430–440; Worthington, R. W., Mulders, M. S., and Van Rensburg, J. J. (1973); *Clostridium perfringens* type D epsilon prototoxin. Some chemical, immunological and biological properties of a highly purified prototoxin; *Onderstepoort. J. Vet. Res.* 40, 143–149). The mature toxin is highly toxic with an $LD_{50}$ in mice of <100 ng when administered intravenously (Payne, D. W., Williamson, E. D., Havard, H., Modi, N., and Brown, J. (1994); Evaluation of a new cytotoxicity assay for *Clostridium perfringens* type D epsilon toxin; *FEMS Microbiol. Lett.* 116, 161–167). As the basis of an alternative assay for epsilon toxin activity, it has been found that the Madin Darby Canine Kidney (MDCK) cell line was sensitive to C. perfringens type D culture filtrates (Knight, P. A., Burnett, C., Whitaker, A. M., and Queminet, J. (1986); The titration of clostridial toxoids and antisera in cell culture; *Develop. biol. Standard.* 64, 129–136). It was demonstrated that the lethal and dermonecrotic effects of the toxin observed in rabbits and its cytopathic activity were all caused by the same entity in epsilon toxin preparations and that all three activities were valid indicators in toxin neutralisation tests (Knight, P. A., Queminet, J., Blanchard, J. H., and Tilleray, J. H. (1990); In vitro tests for the measurement of clostridial toxins, toxoids and antisera. II. Titration of *Clostridium perfringens* toxins and antitoxins in cell culture; *Biologicals.* 18, 263–270). Recently, the development of a new cytotoxicity assay for the determination of the activity of *C. perfringens* type D epsilon toxin based on the sensitivity of the MDCK cell line has been reported (Payne, D. W., Williamson, E. D., Havard, H., Modi, N., and Brown, J. (1994); Evaluation of a new cytotoxicity assay for *Clostridium perfringens* type D epsilon toxin; *FEMS Microbiol. Lett.* 116, 161–167). In four out of five samples between 15–22 ng/ml of purified epsilon toxin was sufficient to reduce the viability of MDCK cells by 50% and as little as 8 ng/ml sufficient to cause a significant reduction in the viability of the MDCK cells, Payne et al., 1994.

The etx gene encoding epsilon toxin is carried out on an episome distinct from the 3.6Mb chromosome (Canard, B., Saint Joanis, B., and Cole, S. T. (1992); Genomic diversity and organization of virulence genes in the pathogenic anaerobe *Clostridium perfringens. Mol. Microbiol.* 6, 1421–1429). The gene has been cloned and sequences for both B and D types determined. The cloned gene etxB coded for a protein of $M_r$~32,981 (Hunter, S. E., Clarke, I. N., Kelly, D. C., and Titball, R. W. (1992); Cloning and nucleotide sequencing of the *Clostridium perfringens* epsilontoxin gene and its expression in *Escherichia coli; Infect. Immun.* 60, 102–110). Neither the sequenced gene or the derived protein showed homology with other proteins. Comparison of the sequences of cloned etx genes from type B and type D strains revealed two nucleotide differences in the open reading frame resulting in one amino acid substitution (Havard, H. L., Hunter, S. E., and Titball, R. W. (1992); Comparison of the nucleotide sequence and development of a PCR test for the epsilon toxin gene of *Clostridium perfringens* type B and type D; *FEMS Microbiol. Lett.* 76, 77–81). The promoters for the genes were not homologous, with different putative –10 and –35 sequences. This allowed the development of epsilon-specific PCR primers to produce a system for typing B and D strains of C. perfringens. The etx promoter allowed expression of the cloned gene in *E. coli* (Hunter et al., 1992). Epsilon toxin is preceded by a signal peptide resulting in the native protein being exported from *C. perfringens* and the recombinant protein accumulating in the periplasmic space of *E. coli* (Hunter et al., 1992; Bullen, J. J. and Batty, I. (1956); The effect of *Clostridium welchii* type D culture filtrates on the permeability of the mouse intestine; *J. Pathol. Bacteriol.* 71, 311–323). The recombinant toxin expressed in *E. coli* was shown to have identical biochemical and biological properties to those of the native toxin.

Epsilon prototoxin produced in the gut of animals is activated by proteolytic enzymes present in intestinal fluid (Niilo, L. (1965); Bovine enterotoxaemia.III; Factors affecting the stability of the toxins of *Clostridium perfringens* types A, C and D; *Can. Vet. J.* 6, 38–42). The mature toxin increases intestinal permeability and enters the blood supply (Bullen and Batty, 1956; Bullen, J. J. (1970); Role of toxins in host-parasite relationships. *In Micribial toxins volume* 1. S. Ajl, S. Kadis, and T. C. Montie, eds. (New York: Academic Press), pp. 233–276; Jansen, B. C. (1967); The production of a basic immunity against pulpy kidney disease; *Onderstepoort. J. Vet. Res.* 34, 65–80. The mode of action of epsilon toxin is not known, but several observations have suggested that it acts upon the central nervous system. The toxin rapidly causes a widespread disturbance in the permeability balance of the brain by disrupting vascular endothelia (Finnie, J. W. (1984); Ultrastructural changes in the brain of mice given *Clostridium perfringens* type D epsilon toxin; *J. Comp. Pathol.* 94, 445–452; Buxton, D. (1976); Use of horseradish peroxidase to study the antagonism of *Clostridium welchii* (*Cl. perfringens*) type D epsilon toxin in mice by the formalinized epsilon prototoxin; *J. Comp. Pathol.* 86, 67–72). As degenerative changes progress, serum proteins and eventually red cells leak from the vasculature, astrocyte end feet rupture and oedema ensues (Buxton, D. and Morgan, K. T. (1967); Studies of the lesions produced in the brains of colostrum deprived lambs by *Clostidium welchii* (*Clostridium perfringens*) type D toxin; *J. Comp. Path.* 86, 435–447). In acute cases of epsilon toxin induced entertoxaemia characteristic lesions occur at specific sites in the brain (Hartley, 1956; Buxton, 1976; McDonel, 1986). Chemical modification experiments have demonstrated the importance of certain amino acid residues for the lethality of epsilon toxin. One tryptophan (Sakurai, J. and Nagahama, M. (1985); Role of one tryptophan residue in the lethal activity of *Clostridium perfringens* epsilon toxin; *Biochem. Biophys. Res. Commun.* 128, 760–766), one histidine (Sakurai, J. and Nagaharna, M. (1987); Carboxyl groups in *Clostridium perfringens* epsilon toxin; *Microb. Pathog.* 3, 469–474), one tyrosine (Sakurai, J. and Nagahama, M. (1987); The inactivation of *Clostridium perfringens* epsilon toxin by treatment with tetranitromethane and N-acetylimidazole; *Toxicon* 25, 279–284) and three or four aspartic or glutamic acids (Sakurai, J. and Nagahama, M. (1987); Histidine residues in *Clostridium perfringens* epsilon toxin; *FEMS Microbiology Letters* 41, 317–319) residues were shown to be essential for the lethal effect of epsilon toxin. Eight lysine residues have also been shown to be important in activity, but are probably involved in maintaining conformation rather than being integral to an active site (Sakurai, J. and Nagahama, M. (1986); Amino groups in *Clostridium perfringens* epsilon prototoxin and epsilon toxin. *Microb. Pathog.* 1, 417–423).

It is an object of the present invention to provide novel polypeptides for use in vaccines which are capable of inducing protective antibodies directed against *C. perfringens* epsilon toxin when administered to animals or man and thereby providing prophylaxis or therapy against infection by *C. perfringens* epsilon toxin.

The present invention provides a polypeptide capable of producing an immune response which is protective against *Clostridium perfringens*, said polypeptide comprising an amino acid sequence which has at least 60% homology with the amino acid sequence of *Clostridium perfringens* epsilon toxin or an immunogenic fragment thereof, characterised in that the amino acid residue corresponding to residue 106 of the mature toxin is of an amino acid other than histidine.

Suitably, the polypeptide has an amino acid sequence which has at least 80% homology and preferably 90% homology and is most preferably substantially completely homologous with the amino acid sequence of *Clostridium perfringens* epsilon toxin or an immunogenic fragment thereof.

The amino acid sequence of *Clostridium perfringens* epsilon toxin is shown hereinafter in as amino acids 1–283 of FIG. 2 (SEQ ID No 2). Where the polypeptide of the invention is homologous to that of SEQ ID No 2 or an immunogenic fragment thereof, it is preferable that any altered amino acids are replaced by conservative substitutions.

By 'conservative substitution' is meant the substitution of an amino acid by another one of the same class; the classes being as follows:

| CLASS | EXAMPLES OF AMINO ACID |
|---|---|
| Nonpolar: | Ala, Val, Leu, Ile, Pro, Met, Phe, Trp |
| Uncharged polar: | Gly, Ser, Thr, Cys, Tyr, Asn, Gln |
| Acidic: | Asp, Glu |
| Basic: | Lys, Arg, His |

As is well known to those skilled in the art, altering the primary structure of a peptide by a conservative substitution may not significantly alter the a ctivity of that peptide because the side-chain of the amino acid which is inserted into the sequence may be able to form sim ilar bonds and contacts as the side chain of the amino acid which has been substituted out. This is so even when the substitution is in a region which is critical in determining the peptides conformation.

Non-conservative substitutions are possible provided that these do not interupt with the immunogenicity of the polypeptide.

The expression "immunogenic fragment" used herein refers to a polypeptide which is shorter than full length native toxin, but which includes at least one antigenic determinant and also which includes a residue corresponding to residue 106 of the mature toxin. Suitably the fragments will comprise at least 15, more suitably at least 30 and preferably a t least 60 amino acids.

In particular, the polypeptide comprises a protein which has an amino acid sequence which has at least 60% homology with the amino acid sequence of *Clostridium perfringens* epsilon toxin characterised in that the amino acid residue corresponding to residue 106 of the mature toxin is of an amino acid other than histidine.

Most preferably the protein comprises the amino acid sequence of clostridium perfringens epsilon toxin and is characterised in that the amino acid residue corresponding to residue 106 of the mature toxin is of an amino acid other than histidine.

Preferably the amino acid at position 106 is a non-basic amino acid, and in particular a non polar amino acid, especially proline.

The polypeptides or proteins of the invention are genetically toxoided (inactivated) which means that they are less likely to cause unwanted side effects in animals to which they are administered. This is a much more precise and quantifiable way of inactivating the toxin rather than using chemical toxoiding methods.

It should also be stressed that the invention also encompasses peptides comprising the amino acid sequences described above i.e. wherein the N- or C- terminus has been extended. Extension of the peptides above may confer additional desirable properties on them, for instance, easier separation or purification, or enhancing or adding to the immunity or labelling.

In particular, the polypeptide or protein described above may form part of a fusion protein which may further comprise a moiety which confers these additional properties. For example, the amino acid sequence of glutathione-S-transferase may be included or A non-C. perfringens antigenic protein may be included fused to the protein of the invention for the purpose of providing other immunity or labelling. Alternatively the polypeptide or protein of the invention may be in the form of a conjugate with another protein which confers such an additional desirable property.

The polypeptides of the invention may be prepared synthetically, or more suitably, they are obtained using recombinant DNA technology. Thus the invention further provides a nucleic acid which encodes a polypeptide as described above.

Suitably, the nucleic acid comprises the part of the sequence shown in SEQ ID No 5 which encodes the SEQ ID no 6.

Such nucleic acids may be incorporated into an expression vector, such as a plasmid, under the control of a promoter as understood in the art. The vector may include other structures as conventional in the art, such as signal sequences, leader sequences and enhancers, and can be used to transform a host cell, for example a prokaryotic cell such as *E. coli* or a eukaryotic cell. Transformed cells can then be cultured and polypeptide of the invention recovered therefrom, either from the cells or from the culture medium, depending upon whether the desired product is secreted from the cell or not.

In a further aspect of the invention there is provided a method for inducing an immune response protective against *Clostridium perfringens* epsilon toxin in a mammal, said method comprising administering to said mammal an polypeptide as described above.

Suitable mammals include humans and animals, such as sheep, lambs and goats.

The polypeptide may be administered to the mammal directly, for example in the form of a vaccine composition. Alternatively, a nucleic acid encoding it may be incorporated into a suitable vaccine vector, for example an attenuated live virus vaccine carrier under the control of suitable promoters etc. to ensure that the vector expresses the polypeptide in situ. Administration of the vector to the mammal thereby produces the desired immune response. Suitable vectors will be apparent to the skilled person. They may include vaccinia virus vectors, such as the Lister strain, or attenuated gut-colonising microorganisms such as attenuated strains of Salmonella.

In a further embodiment the present invention provides vaccine compositions comprising the polypeptides or proteins of the invention or as an alternative, a vector capable of expressing said polypeptide or protein, suitably in appropriate dosage units. The compositions are optionally complemented as necessary by further agents for optimising protection eg adjuvants and carriers, preferably pharmaceutically acceptable carriers and adjuvants. Freunds incomplete or complete adjuvant or alhydrogel may be used as typical adjuvants, but other suitable candidates such as those described in WO 9203164 may be used. Carrier function may be fulfilled by saline solutions. The carrier may be one suited to parenteral administration, particularly intraperitoneal administration but optionally oral for example in a live vaccine vector such as an attenuated gut-colonising microorganism, or administration in the form of droplets or capsules, such as liposomes or microcapsules as would be effective in delivering the composition to the airways of an individual for the purpose of evoking a mucosal immune response.

The microcapsule may comprise biodegradable polymers for example polylactic acid either with or without glycolic acid or with or without a block co-polymer which may contain the following repeat unit: (POP-POE)$_n$ where POP is polyoxypropylene and POE is polyoxyethylene. Block co-polymers which contain (POP-POE)$_n$ may be of particular use.

The proteins and fusion proteins of the present invention may be used as mucosal adjuvants. They may be co-administered with a non-C. perfringens antigenic protein—this may augment the mucosal immune response to the non-*C. perfringens* antigenic protein. There is evidence that epsilon toxin binds to a cell surface receptor in Payne et al 1994.

The invention will now be described with reference to the following diagrams and sequences by way of example only:

FIGURES

FIG. 1 illustrates constructs of the present invention;

SEQUENCES

SEQ ID No. 1 shows the nucleic acid sequence and corresponding amino acid sequence of the *C. perfringens* epsilon toxin gene. Amino acids −45 to −14 corresponds to the signal sequence. Amino acids −13 to −1 correspond to the prototoxin cleared by trypsin to produce active mature toxin. Amino acids 1–283 correspond to the mature toxin;

SEQ ID No. 2 shows the amino acids of SEQ ID NO. 1.

SEQ ID NO 3 represents the nucleic acid sequence and corresponding amino acid sequence of the mutated *C. perfringens* epsilon toxin gene in SDM10 wherein amino acid 106 of the mature toxin has been replaced by a proline;

SEQ ID NO 4 corresponds to amino acids of SEQ ID No 3.

SEQ ID No 5 represents the nucleic acid sequence of the *C. perfringens* epsilon toxin gene wherein the bases that code for amino acid 106 (bases 451–453) of the mature protein are represented by NNN; and SEQ ID NO 6 represents the mature toxin part of the *C. perfringens* epsilon toxin gene wherein amino acid 106 is denoted Xaa indicating that this amino acid may be any amino acid except histidine.

EXAMPLE 1

Production of Mutants

Mutants with single amino acid changes were constructed using oligonucleotide site directed mutagenesis. The epsilon toxin gene was supplied for site-directed mutagenesis in pBluescript II KS +/− and the mutated genes were delivered in this vector. The mutated gene was subcloned into pGEX3a, the epsilon toxin being expressed as a fusion with glutathione-S-transferase, and into pTrc99A, the epsilon toxin being expressed at high levels under the control of the trc promoter. These constructs are represented in FIG. 1. The mutant with the mutation converting the histidine residue at position 106 to a proline is referred to as SDM10.

EXAMPLE 2

Immunisation of Mice

Groups of thirty mice were immunised intraperitoneally in Incomplete Freund's adjuvant (IFA) with epsilon toxoid, purified GST-epsilon fusion expressed by pGEXhlh2, purified GST-SDM10 fusion expressed by pGEXhlh2.10, or SDM10 periplasmic preparation expressed by pTrcEP7.10. Each dose was equivalent to 0.27 nM of toxoid. Two control groups were included: mice immunised with 0.27 nM GST (Sigma) in IFA and unimmunised mice. Mice were boosted on days 21 and 35. Ten mice per group were bled on day 48 and the sera were titred against recombinant epsilon toxin and epsilon toxin from *C. perfringens* 8346.

On day 54 the mice were challenged in groups of 6 mice with 10–10$^3$ LD$_{50}$ doses of recombinant epsilon toxin, administered i.v. The mice were observed for 24 h and times to death were noted.

Mice immunised with epsilon toxoid, GST-epsilon, GST-10 and SDM10 were fully protected against an intravenous challenge of up to 100 LD$_{50}$ doses of toxin per mouse. All control mice died.

When the challenge dose was raised to 1000 LD$_{50}$ per mouse, mice immunised with toxoid or with SDM10 survived. Five of six mice survived this level of challenge in the GST-10 and GST-epsilon groups.

Thus the polypeptides of the invention are as protective as the toxoid.

What is claimed is:

1. A purified polypeptide capable of producing an immune response which is protective against *Clostridium perfringens*, said polypeptide comprising an amino acid sequence as shown in SEQ ID NO:4.

2. The polypeptide according to claim 1, further being fused to glutathione-S-transferase.

3. A purified polypeptide capable of producing an immune response which is protective against *Clostridium perfringens*, said polypeptide comprising an amino acid sequence indicated as 1–283 of SEQ ID NO:2, wherein the amino acid residue corresponding to residue 106 as shown in SEQ ID NO:2 is proline.

* * * * *